US011319554B2

(12) United States Patent
Cha et al.

(10) Patent No.: US 11,319,554 B2
(45) Date of Patent: May 3, 2022

(54) CUCUMBER MOSAIC VIRUS RESISTANT PEPPER PLANTS

(71) Applicant: Seminis Vegetable Seeds, Inc., St. Louis, MO (US)

(72) Inventors: Jaecheol Cha, Cheongju (KR); Hongmo Kim, Yongin-si (KR); Joel M. Kniskern, Sacramento, CA (US); Sanghyeon Nam, Cheongju-si (KR); Alexandria E. Quezada, Woodland, CA (US); Vijay Vontimitta, Bangalore (IN)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 9 days.

(21) Appl. No.: 16/649,135

(22) PCT Filed: Sep. 28, 2018

(86) PCT No.: PCT/US2018/053444
§ 371 (c)(1),
(2) Date: Mar. 19, 2020

(87) PCT Pub. No.: WO2019/067914
PCT Pub. Date: Apr. 4, 2019

(65) Prior Publication Data
US 2020/0291422 A1    Sep. 17, 2020

Related U.S. Application Data

(60) Provisional application No. 62/566,310, filed on Sep. 29, 2017.

(51) Int. Cl.
*C12N 15/82* (2006.01)
*A01H 1/04* (2006.01)
*A01H 5/08* (2018.01)

(52) U.S. Cl.
CPC .......... *C12N 15/8283* (2013.01); *A01H 1/04* (2013.01); *A01H 5/08* (2013.01)

(58) Field of Classification Search
None
See application file for complete search history.

(56) References Cited

U.S. PATENT DOCUMENTS

2011/0138493 A1    6/2011   Copes et al.

FOREIGN PATENT DOCUMENTS

WO        2001084912 A2    11/2001

OTHER PUBLICATIONS

Eun et al 2016 Hortic. Enrviron. Biotechnol. 57:589-597, provided by Applicant (Year: 2016).*

Yao et al 2013 Euphytica 193:135-145, provided by Applicant (Year: 2013).*

Kang et al., "Molecular mapping and characterization of a single dominant gene controlling CMV resistance in peppers (*Capsicum annuum* L.)," Theor Appl Genet., 2010, 120,1587-1596.

Ben Chaim et al.,"Identification of quantitative trait loci associated with resistance to cucumber mosaic virus in *Capsicum annuum*," Theor Appl Genet.,2001, 102, 1213-1220.

Min et al., "Developmental Changes of Recessive Genes-mediated Cucumber mosaic virus (CMV) Resistance in Peppers (*Capsicum annuum* L.)," Kor. J. Hort. Sci. Technol., 2014, 32(2), 235-240.

Guo et al., "Rapid identification of QTLs underlying resistance to Cucumber mosaic virus in pepper (*Capsicum frutescens*)," Theor Appl Genet., 2017, 130, 41-52.

Paran et al., "An integrated genetic linkage map of pepper (*Capsicum* spp.)," Molecular Breeding, 2004, 13, 251-261.

"AC243705: *Solanum lycopersicum* strain Heinz 1706 chromosome 1 clone slm-16n20 map 1," NCBI GenBank, Accession No. AC243705.9, Jul. 15, 2014 (Jul. 15, 2014), pp. 1-3. Retrieved from the Internet<https://www.ncbi.nlm.nih.gov/nuccore/AC243705> on Nov. 8, 2018.

Ashrafi et al. "De Novo Assembly of the Pepper Transcriptome (*Capsicum annuum*): a Benchmark for in Silico Discovery of SNPs, SSRs and candidate genes," BMC Genomics, Oct. 30, 2012 (Oct. 30, 2012), vol. 13, No. 571, pp. 1-15.

Eun et al. "QTL Mapping of Resistance to the Cucumber Mosaic Virus P1 Strain in Pepper Using a Genotyping-by-Sequencing Analysis," Horticulture, Environment, and Biotechnology, Dec. 1, 2016 (Dec. 1, 2016), vol. 57, No. 6, pp. 589-597.

Lee et al. "Transgenic Peppers that are Highly Tolerant to a New CMV Pathotype," Plant Cell Reports, Feb. 1, 2009 (Feb. 1, 2009), vol. 28, No. 2, pp. 223-232.

Shi et al. "Inheritance and QTL mapping of cucumber mosaic virus resistance in cucumber (*Cucumis sativus* L.)," PLoS One, Jul. 18, 2018 (Jul. 18, 2018), vol. 13, Iss. 7, pp. 1-12. entire document.

Tan et al. "A Comparative Testing of Cucumber mosaic virus (CMV)-Based Constructs to Generate Virus Resistant Plants," American Journal of Plant Sciences, Apr. 1, 2012 (Apr. 1, 2012), vol. 3, pp. 461-472. entire document.

Yao et al. "Genetic analysis and identification of QTLs for resistance to cucumber mosaic virus in chili pepper (*Capsicum annuum* L.)," Euphytica, Jun. 15, 2013 (Jun. 15, 2013), vol. 193, No. 2, pp. 135-145.

International Search Report and Written Opinion regarding International Applicaiton No. PCT/US2018/053444, dated Dec. 10, 2018.

* cited by examiner

*Primary Examiner* — Brent T Page
(74) *Attorney, Agent, or Firm* — Dentons US LLP; Matthew Madsen

(57) ABSTRACT

The present disclosure provides *Capsicum annuum* plants exhibiting increased resistance to resistance-breaking cucumber mosaic virus (rbCMV) strains. Such plants comprise novel introgressed genomic regions associated with disease resistance on chromosome 8. In certain aspects, compositions and methods for producing, breeding, identifying, and selecting plants or germplasm with an increased disease resistance phenotype are provided.

20 Claims, 3 Drawing Sheets

Specification includes a Sequence Listing.

SEQUENCE LISTING

<160> NUMBER OF SEQ ID NOS: 20

<210> SEQ ID NO 1
<211> LENGTH: 27
<212> TYPE: DNA
<213> ORGANISM: Artificial sequence
<220> FEATURE:
<223> OTHER INFORMATION: PCR primer

<400> SEQUENCE: 1
ggttggtttg ctaaatgttg agggtta                                27

<210> SEQ ID NO 2
<211> LENGTH: 24
<212> TYPE: DNA
<213> ORGANISM: Artificial sequence
<220> FEATURE:
<223> OTHER INFORMATION: PCR primer

<400> SEQUENCE: 2
cccaggctta atgaaacctt cttc                                   24

<210> SEQ ID NO 3
<211> LENGTH: 20
<212> TYPE: DNA
<213> ORGANISM: Artificial sequence
<220> FEATURE:
<223> OTHER INFORMATION: Probe

<400> SEQUENCE: 3
ctttgcttac actatttgac                                        20

<210> SEQ ID NO 4
<211> LENGTH: 18
<212> TYPE: DNA
<213> ORGANISM: Artificial sequence
<220> FEATURE:
<223> OTHER INFORMATION: Probe

<400> SEQUENCE: 4
ttgcttacac tgtttgac                                          18

<210> SEQ ID NO 5
<211> LENGTH: 149
<212> TYPE: DNA
<213> ORGANISM: Capsicum annuum

<400> SEQUENCE: 5
ggttggtttg ctaaatgttg agggttatta caactctttg cttacactrt ttgacaatgg    60
tgttgaagaa ggtttcatta agcctggggc tcgtgacatt gttcttgctg ctcctacagc   120
cagagagctt ttaagcaaga tggaggtac                                    149

<210> SEQ ID NO 6
<211> LENGTH: 28
<212> TYPE: DNA
<213> ORGANISM: Artificial sequence
<220> FEATURE:
<223> OTHER INFORMATION: PCR primer

<400> SEQUENCE: 6
tcagttggat ctcatttaaa tgcactag                               28

```
<210> SEQ ID NO 7
<211> LENGTH: 20
<212> TYPE: DNA
<213> ORGANISM: Artificial sequence
<220> FEATURE:
<223> OTHER INFORMATION: PCR primer

<400> SEQUENCE: 7
ttctgaagag cggtgttgct                                                      20

<210> SEQ ID NO 8
<211> LENGTH: 21
<212> TYPE: DNA
<213> ORGANISM: Artificial sequence
<220> FEATURE:
<223> OTHER INFORMATION: Probe

<400> SEQUENCE: 8
aattggcaag tactactatt a                                                    21

<210> SEQ ID NO 9
<211> LENGTH: 18
<212> TYPE: DNA
<213> ORGANISM: Artificial sequence
<220> FEATURE:
<223> OTHER INFORMATION: Probe

<400> SEQUENCE: 9
tggcaagtac tgctatta                                                        18

<210> SEQ ID NO 10
<211> LENGTH: 201
<212> TYPE: DNA
<213> ORGANISM: Capsicum annuum

<400> SEQUENCE: 10
actaagacaa tgggctgcag caaagttgaa gacatttta tcagttggat ctcatttaaa           60
tgcactagat tttctaaccg tcggccaatt ggcaagtact rctattaagc aacaccgctc         120
ttcagaaggt atcaataaaa gatgcagaaa agaccacttt gagctacttg taatacttta         180
cccagtacaa gaagtattac a                                                  201

<210> SEQ ID NO 11
<211> LENGTH: 29
<212> TYPE: DNA
<213> ORGANISM: Artificial sequence
<220> FEATURE:
<223> OTHER INFORMATION: PCR primer

<400> SEQUENCE: 11
ggaatagcat cagaaattat caaggcaaa                                            29

<210> SEQ ID NO 12
<211> LENGTH: 20
<212> TYPE: DNA
<213> ORGANISM: Artificial sequence
<220> FEATURE:
<223> OTHER INFORMATION: PCR primer

<400> SEQUENCE: 12
ccgctgcgct actctgattt                                                      20
```

```
<210> SEQ ID NO 13
<211> LENGTH: 20
<212> TYPE: DNA
<213> ORGANISM: Artificial sequence
<220> FEATURE:
<223> OTHER INFORMATION: Probe

<400> SEQUENCE: 13
agccaacatt tggtatcaga                                                    20

<210> SEQ ID NO 14
<211> LENGTH: 20
<212> TYPE: DNA
<213> ORGANISM: Artificial sequence
<220> FEATURE:
<223> OTHER INFORMATION: Probe

<400> SEQUENCE: 14
agccaacatt tgatatcaga                                                    20

<210> SEQ ID NO 15
<211> LENGTH: 201
<212> TYPE: DNA
<213> ORGANISM: Capsicum annuum

<400> SEQUENCE: 15
aaaaattcat aaatctgaaa atcggaattc catattttt tttttaacaa atggaatagc         60
atcagaaatt atcaaggcaa atgtattgat ggctctgata ycaaatgttg gctgaaaaat       120
cagagtagcg cagcggaaat atggaataca catacctcca gccattgttg aggatctgta       180
gttgatgtcg gagtcaacta a                                                 201

<210> SEQ ID NO 16
<211> LENGTH: 301
<212> TYPE: DNA
<213> ORGANISM: Zea mays
<220> FEATURE:
<221> NAME/KEY: misc_feature
<222> LOCATION: (166)..(166)
<223> OTHER INFORMATION: n is a, c, g, or t

<400> SEQUENCE: 16
gagagtttgt actatcattt atacttgaaa cttgtttact cacttgaatt tccctaattc        60
tgtcgctgat gaaaccagcg ttcctctccg ctctgatgat ttccttttct gtcaattcac       120
ctacttcttc caccttccct gataacatat yggaggaacaa tcagcnatcg gtgactagat     180
tggtttagtt aactgataca tattctatcg atactctaaa gggccggggt tatacgacat       240
atccggtgtg gaagtttagg cctaccatat ctcttttgca tcttcatgag caagggtcca       300
a                                                                      301

<210> SEQ ID NO 17
<211> LENGTH: 24
<212> TYPE: DNA
<213> ORGANISM: Artificial sequence
<220> FEATURE:
<223> OTHER INFORMATION: Primer

<400> SEQUENCE: 17
cctacttctt ccaccttccc tgat                                               24
```

```
<210> SEQ ID NO 18
<211> LENGTH: 28
<212> TYPE: DNA
<213> ORGANISM: Artificial sequence
<220> FEATURE:
<223> OTHER INFORMATION: Primer

<400> SEQUENCE: 18
cagttaacta aaccaatcta gtcaccga                                          28

<210> SEQ ID NO 19
<211> LENGTH: 20
<212> TYPE: DNA
<213> ORGANISM: Artificial sequence
<220> FEATURE:
<223> OTHER INFORMATION: Probe

<400> SEQUENCE: 19
tgattgttcc tcaatatgtt                                                   20

<210> SEQ ID NO 20
<211> LENGTH: 18
<212> TYPE: DNA
<213> ORGANISM: Artificial sequence
<220> FEATURE:
<223> OTHER INFORMATION: Probe

<400> SEQUENCE: 20
attgttcctc gatatgtt                                                     18
```

CUCUMBER MOSAIC VIRUS RESISTANT PEPPER PLANTS

REFERENCE TO RELATED APPLICATION

This application is a 371 National Stage application of International Application No. PCT/US2018/053444, filed Sep. 28, 2018, which claims the benefit of United States Provisional Application No. 62/566,310, filed Sep. 29, 2017, which are incorporated herein by reference in their entireties.

INCORPORATION OF SEQUENCE LISTING

The sequence listing that is contained in the file named "SEMB030WO_ST25.txt", which is 8 kilobytes as measured in Microsoft Windows operating system and was created on Sep. 27, 2018, is filed electronically herewith and incorporated herein by reference.

FIELD OF THE INVENTION

The present invention relates to the field of agriculture and more specifically to methods and compositions for producing pepper plants exhibiting improved resistance to a broad range of cucumber mosaic virus (CMV) strains, and in particular improved resistance against resistance-breaking CMV (rbCMV) strains that are infectious on pepper lines with the dominant CMV resistance locus on chromosome 2, often referred to as cmr-1.

BACKGROUND OF THE INVENTION

Disease resistance is an important trait in agriculture, particularly for the production of food crops. Although disease resistance alleles have been identified in pepper plants, efforts to introduce these alleles into cultivated lines are hindered by a lack of specific markers linked to the alleles, linkage drag that leads to unacceptable plant quality and a lack of broad spectrum resistance. The use of marker-assisted selection (MAS) in plant breeding methods has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis and an often incomplete understanding of the genetic background underlying expression of a desired phenotype.

SUMMARY OF THE INVENTION

The present disclosure provides a cultivated variety of a *Capsicum annuum* plant comprising an introgressed allele on chromosome 8 that confers increased resistance to resistance-breaking cucumber mosaic virus (CMV) strains relative to a plant lacking the introgression. In certain embodiments the introgressed allele is flanked by Marker1 (SEQ ID NO:5) and Marker4 (SEQ ID NO:16) in the plant. In further embodiments the introgressed allele is located between 32,904,383 bp and 2,992,472 bp of chromosome 8 in public pepper genome sequence Pepper.CM334v1.55. In other embodiments the resistance comprises resistance to CMV isolate "Bucheon." In particular embodiments the plant is homozygous for the introgressed allele. In additional embodiments the introgressed allele comprises the resistance haplotype of HAS-ZF17-4448, wherein a sample of seed comprising the resistance haplotype was deposited under ATCC Accession Number PTA-124434.

The present disclosure also provides a seed that produces a cultivated variety of a *Capsicum annuum* plant comprising an introgressed allele on chromosome 8 that confers increased resistance to resistance-breaking cucumber mosaic virus (CMV) strains relative to a plant lacking the introgression.

Additionally, the present disclosure provides a plant part of a cultivated variety of a *Capsicum annuum* plant comprising an introgressed allele on chromosome 8 that confers increased resistance to resistance-breaking cucumber mosaic virus (CMV) strains relative to a plant lacking the introgression. In certain embodiments the plant part is a cell, a seed, a root, a stem, a leaf, a fruit, a flower, or pollen.

The present disclosure further provides a method for producing a cultivated variety of a *Capsicum annuum* plant with improved resistance to resistance-breaking cucumber mosaic virus (CMV) strains, comprising introgressing into the plant a chromosomal segment from chromosome 8 that confers resistance to resistance-breaking cucumber mosaic virus (CMV) strains relative to a plant lacking the introgression. In some embodiments the introgressing comprises crossing a plant comprising the chromosomal segment with itself or with a second *Capsicum annuum* plant of a different genotype to produce one or more progeny plants, and selecting a progeny plant comprising the chromosomal segment. In other embodiments selecting a progeny plant comprises detecting at least one allele flanked by Marker1 (SEQ ID NO:5) and Marker4 (SEQ ID NO:16) on chromosome 8. In yet other embodiments selecting comprises detecting Marker1 (SEQ ID NO:5) or Marker4 (SEQ ID NO:16). In further embodiments the progeny plant is an $F_2$-$F_6$ progeny plant. In particular embodiments the crossing comprises backcrossing, which in certain embodiments comprises from 2-7 generations of backcrosses. In selected embodiments the introgressed allele comprises the resistance haplotype of HAS-ZF17-4448, wherein a sample of seed comprising the resistance haplotype was deposited under ATCC Accession Number PTA-124434.

The present disclosure additionally provides a *Capsicum annuum* plant produced by a method comprising introgressing into the plant a chromosomal segment from chromosome 8 that confers resistance to resistance-breaking cucumber mosaic virus (CMV) strains relative to a plant lacking the introgression. Thus, the present disclosure also provides a method of producing food or feed comprising obtaining a cultivated variety of a *Capsicum annuum* plant comprising an introgressed allele on chromosome 8 that confers increased resistance to resistance-breaking cucumber mosaic virus (CMV) strains relative to a plant lacking the introgression, or a part thereof, and producing the food or feed from the plant or part thereof.

The present disclosure further provides a *Capsicum annuum* plant obtainable by a method comprising the step of introgressing into a plant a resistance to resistance-breaking cucumber mosaic virus (CMV) strains allele, wherein the resistance allele is defined as located in a genomic region flanked by Marker1 (SEQ ID NO:5) and Marker4 (SEQ ID NO:16) on chromosome 8. In certain embodiments the introgressing comprises backcrossing. In other embodiments the introgressing comprises marker-assisted selection. In yet other embodiments the introgressing comprises assaying for the resistance to resistance-breaking cucumber mosaic virus (CMV) strains.

The present disclosure also provides a method of selecting a *Capsicum annuum* plant exhibiting resistance to resistance-breaking cucumber mosaic virus (CMV) strains, comprising crossing a cultivated variety of a *Capsicum annuum* plant comprising an introgressed allele on chromosome 8 that confers increased resistance to resistance-breaking cucumber mosaic virus (CMV) strains relative to a plant lacking the introgression with itself or with a second *Capsicum annuum* plant of a different genotype to produce one or more progeny plants, and selecting a progeny plant comprising the introgressed allele. In certain embodiments selecting the progeny plant comprises identifying a genetic marker genetically linked to the introgression. In additional embodiments selecting the progeny plant comprises identifying a genetic marker within or genetically linked to a genomic region flanked in the genome of the plant by Marker1 (SEQ ID NO:5) and Marker4 (SEQ ID NO:16) on chromosome 8. In particular embodiments selecting comprises detecting Marker1 (SEQ ID NO:5) or Marker4 (SEQ ID NO:16). In further embodiments the progeny plant is an $F_2$-$F_6$ progeny plant. In yet further embodiments producing the progeny plant comprises backcrossing.

BRIEF DESCRIPTION OF THE DRAWINGS

FIG. 2: Disease scores comparisons between germplasm of varying genetic background and tested against different CMV isolates. The disease score is measured on a scale of 1-9, where 1 is fully resistant and 9 is fully susceptible.

DETAILED DESCRIPTION

Figure 1:
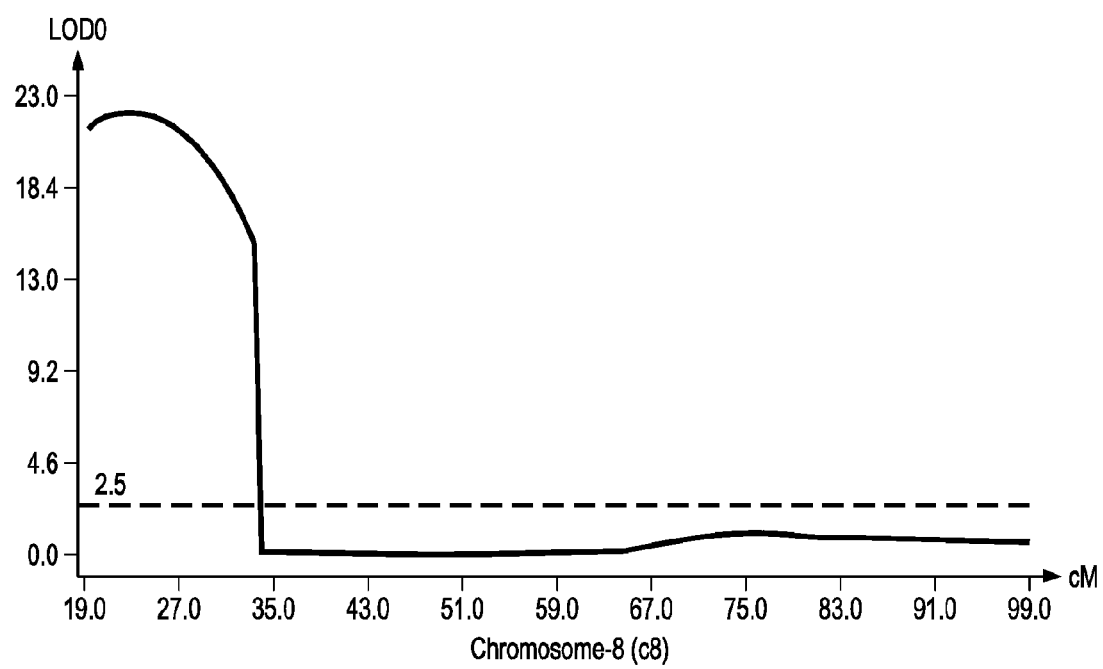
FIG. 1: The genomic region providing resistance to rbCMV was mapped to the proximal end of chromosome 8.
Figure 1:

Cucumber mosaic virus (CMV) has one of the broadest host ranges of any virus throughout the temperate regions of the world. More than 800 species of plant can be infected, and more than 60 aphid species are vectors for this virus. CMV is a member of the cucumovirus group and is highly diverse. More than 60 strains of CMV have been identified. CMV is known to infect economically important plants, such as tomato, cucumber, potato, tobacco and pepper.

Previously, CMV resistance sources have been identified in pepper. Several studies have attempted to unravel the genetics for these resistance sources. Depending on the source, loci are reported to be located on multiple linkage groups. The genetic control of these loci differs and is highly source dependent. For source BJ0747 loci were identified on linkage groups 4, 7, 8 and 16, but control of the CMV resistance could not be attributed to a single locus leading to the conclusion that CMV resistance was a complex polygenic trait. Similarly, the CMV resistance of pepper line 'Perennial' is controlled by multiple loci, although these loci were mapped to different linkage groups, namely LG4, 6, and 11. In contrast, only one case of single locus dominant resistance is known. This locus is located on chromosome 2. The locus on chromosome 2, often referred to as cmr-1, is widely used by breeding companies to ensure CMV resistance for their material. However, recent studies show that the dominant locus on chromosome 2 provide imperfect resistance to newly discovered CMV isolates. These resistance-breaking (rbCMV) strains, often referred to as CMVP1 or $CMV_{P1}$, dominate Korea, are abundant in India, and likely occur in other regions of Asia. However, CMV is a worldwide problem and it cannot be excluded that these resistance-breaking strains might become dominant in other parts of the world. Especially, in regions where resistant pepper varieties are being grown there likely is strong selection for CMV strains that overcome the current resistance genes used by breeders. Many efforts have been made to identify sources that provide adequate resistance against these new resistance-breaking CMV (rbCMV) isolates, but this has proven to be difficult to such an extent that some researchers have relied on genetic modification to develop tolerant pepper varieties. A single recessive gene, called cmr-2, that provides resistance to one rbCMV isolate has been identified on chromosome 1. In addition, two resistance loci against the same rbCMV isolate have been identified and were mapped to LG4 of pepper.

The present invention represents a significant advance in that it provides an internal breeding line ("internal resistant breeding line") that was identified to contain a single QTL that provides broad-spectrum resistance to CMV, including resistance to isolates of CMV that overcome the CMV resistance of the chromosome 2 locus cmr-1 and 'regular non-breaking CMV' isolates. The QTL is located on the proximal end of chromosome 8 between Marker1 and Marker4. Resistance of the QTL was determined to have an additive effect indicating that homozygous deployment is better than heterozygous deployment.

I. Genomic Regions, Alleles, and Polymorphisms Associated with Increased Resistance to Resistance-Breaking Cucumber Mosaic Virus (CMV) Strains The inventors identified a novel QTL on chromosome 8 from an internal resistant breeding line that provide resistance to isolates of rbCMV, such as rbCMV isolate "Bucheon," or CMVP1, that can infect varieties with CMV resistance locus on chromosome 2, as well as resistance to 'regular CMV' (non-resistance breaking) isolates. The best results are observed when the QTL is present as a homozygous trait.

The newly identified QTL on chromosome 8 covers a region of about 18 cM. The newly identified QTL on chromosome 8 is flanked by Marker1 (SEQ ID NO:5), a SNP change [A/G] at 32,904,383 bp on the public genome of Pepper CM334v.1.55 genome, which is available from solgenomics.net, and Marker4 (SEQ ID NO:16), a SNP change [C/T] at 2,992,472 bp on the public genome of Pepper CM334v.1.55. Thus, the present disclosure provides an elite or cultivated pepper plant comprising an introgressed allele on chromosome 8 of an internal resistant breeding line flanked by Marker1 and Marker4 that exhibits resistance to rbCMV.

II. Introgression of Genomic Regions Associated with Disease Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel markers for identifying and tracking introgression of one or more of the genomic regions from a resistance source, which could be any pepper plant, such as the internal resistant breeding line used herein, into cultivated pepper plant lines. HAS-ZF17-4448, a line containing the resistance locus derived from the internal resistant breeding line used herein, has been deposited with the ATCC (see Section V, below). The invention further provides markers for identifying and tracking the novel introgressions disclosed herein during plant breeding.

The present invention provides a newly identified QTL that provides resistance to a resistance-breaking CMV (rbCMV) isolate. As used herein, the term "rbCMV isolate" refers to a CMV isolate capable of causing a disease in a pepper plant that has the widely used CMV resistance allele on chromosome 2, e.g., "Bukang."

Markers within or linked to any of the genomic intervals of the present invention can be used in a variety of breeding efforts that include introgression of genomic regions associated with disease resistance into a desired genetic background. For example, a marker within 30 cM, 25 cM, 20 cM, 16 cM, 15 cM, 10 cM, 5 cM, 2 cM, or 1 cM of a marker associated with disease resistance described herein can be used for marker-assisted introgression of genomic regions associated with a disease resistant phenotype.

Pepper plants comprising one or more introgressed regions associated with a desired phenotype wherein at least 10%, 25%, 50%, 75%, 90%, or 99% of the remaining genomic sequences carry markers characteristic of the germplasm are also provided. Pepper plants comprising an introgressed region comprising regions closely linked to or adjacent to the genomic regions and markers provided herein and associated with resistance to isolates of CMV that can infect the varieties with a dominant CMV resistance locus on chromosome 2, such as the variety "Bukang," and 'regular non-breaking CMV' isolates are also provided.

III. Development of Disease Resistant *Capsicum annuum* Varieties

For most breeding objectives, commercial breeders work within germplasm that is "cultivated type" or "elite." As used herein, "elite" or "cultivated" variety means a variety that has resulted from breeding and selection for superior horticultural performance for use in agriculture. This germplasm is easier to breed because it generally performs well when evaluated for horticultural performance. A number of cultivated pepper types have been developed, which are agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. However, this approach presents significant difficulties due to fertility problems associated with crosses between diverse lines, and negative linkage drag from the non-cultivated parent. For example, non-cultivated pepper lines can provide alleles associated with disease resistance. However, this non-cultivated type may have poor horticultural qualities such as vulnerability to necrosis or low fruit production.

The process of introgressing desirable resistance alleles from non-cultivated lines into elite cultivated lines while avoiding problems with linkage drag or low trait heritability is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. Moreover, the process of introgressing genomic regions from non-cultivated lines can be greatly facilitated by the availability of informative markers.

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked phenotypically or genetically. Thus, Applicants' discovery of accurate markers associated with disease resistance will facilitate the development of pepper plants having beneficial phenotypes. For example, plants and seeds can be genotyped using the markers of the present invention in order to develop varieties comprising desired disease resistance. Moreover, marker-assisted selection (MAS) allows identification of plants which are homozygous or heterozygous for the desired introgression.

Meiotic recombination is essential for plant breeding because it enables the transfer of favorable alleles across genetic backgrounds, the removal of deleterious genomic fragments, and pyramiding traits that are genetically tightly linked. Limited recombination forces breeders to enlarge segregating populations for progeny screens. In the absence of markers breeders must rely on phenotypic evaluation, which is time-consuming, resource-intensive and not reproducible in every environment, particularly for traits like disease resistance. In contrast markers allow a breeder to select those individuals of interest without having to expose the whole population to phenotypic evaluation. The markers provided by the invention offer an effective alternative and therefore represent a significant advance in the art.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among pepper species in a single assay, making it necessary to work with a combination of marker assays, e.g., haplotype assays. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Vegetable breeders use molecular markers to interrogate a crop's genome and classify material based on genetic, rather than phenotypic, differences. Advanced marker technologies are based on genome sequences, the nucleotide order of distinct, polymorphic genotypes within a species. Such platforms enable selection for horticultural traits with markers linked to favorable alleles, in addition to the organization of germplasm using markers randomly distributed throughout the genome. In the past, a priori knowledge of the genome lacked for major vegetable crops that now have been sequenced. Scientists exploited sequence homology, rather than known polymorphisms, to develop marker platforms. Man-made DNA molecules are used to prime replication of genome fragments when hybridized pair-wise in the presence of a DNA polymerase enzyme. This synthesis, regulated by thermal cycling conditions that control hybridization and replication of DNA strands in the polymerase chain reaction (PCR) to amplify DNA fragments of a length dependent on the distance between each primer pair. These fragments are then detected as markers and commonly known examples include AFLP and RAPD. A third technique, RFLP does not include a DNA amplification step. Amplified fragment length polymorphism (AFLP) technology reduces the complexity of the genome. First, through digestive enzymes cleaving DNA strands in a sequence-specific manner. Fragments are then selected for their size and finally replicated using selective oligonucleotides, each homologous to a subset of genome fragments. As a result, AFLP technology consistently amplifies DNA fragments across genotypes, experiments and laboratories.

Polymorphisms comprising as little as a single nucleotide change can be assayed in a number of ways. For example, detection can be made by electrophoretic techniques including a single strand conformational polymorphism (Orita, et al., *Genomics* 8:271-278, 1989), denaturing gradient gel electrophoresis (Myers, E P 0273085), or cleavage fragment length polymorphisms (Life Technologies, Inc., Gaithersburg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al., *Biotechniques* 12:82-87, 1992), or PCR amplification of multiple specific alleles (PAMSA; Dutton and Sommer, *Biotechniques* 11:700-702, 1991).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a *Capsicum annuum* plant a genotype associated with disease resistance, identify a *Capsicum annuum* plant with a genotype associated with disease resistance, and to select a *Capsicum annuum* plant with a genotype associated with disease resistance. In certain embodiments of methods of the invention, polymorphic nucleic acids can be used to produce a *Capsicum annuum* plant that comprises in its genome an introgressed locus associated with disease resistance. In certain embodiments of the invention, polymorphic nucleic acids can be used to breed progeny *Capsicum annuum* plants comprising a locus associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e., for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in *Capsicum annuum* plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al., *Cold Spring Harbor Symp. Quant. Biol.* 51:263-273, 1986; European Patent 50,424; European Patent 84,796; European Patent 258,017; European Patent 237,362; European Patent 201, 184; U.S. Pat. Nos. 4,683,202; 4,582,788; and U.S. Pat. No. 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz, et al., *Genome Res.* 13:513-523, 2003; Cui, et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which *Capsicum annuum* plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite line" or "cultivated line" means any line that has resulted from breeding and selection for superior agronomic performance. An "elite plant" refers to a plant belonging to an elite line. Numerous elite lines are available and known to those of skill in the art of *Capsicum annuum* breeding. An "elite population" is an assortment of elite individuals or lines that can be used to represent the state of the art in terms of agronomically superior genotypes of a given crop species, such as a *Capsicum annuum* line. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, marker assisted selection, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, "resistance locus" means a locus associated with resistance or tolerance to disease. For instance, a resistance locus according to the present invention may, in one embodiment, control resistance or susceptibility to rbCMV and regular non-breaking CMV isolates.

As used herein, "resistance allele" means the nucleic acid sequence associated with resistance or tolerance to disease.

As used herein "resistance" or "improved resistance" in a plant to disease conditions is an indication that the plant is less affected by disease conditions with respect to yield, survivability and/or other relevant agronomic measures, compared to a less resistant, more "susceptible" plant. Resistance is a relative term, indicating that a "resistant" plant survives and/or produces better yields in disease conditions compared to a different (less resistant) plant grown in similar disease conditions. As used in the art, disease "tolerance" is sometimes used interchangeably with disease "resistance." One of skill will appreciate that plant resistance to disease conditions varies widely, and can represent a spectrum of more-resistant or less-resistant phenotypes. However, by simple observation, one of skill can generally determine the relative resistance or susceptibility of different plants, plant lines or plant families under disease conditions, and furthermore, will also recognize the phenotypic gradations of "resistant."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

V. Deposit Information

A deposit was made of at least 2500 seeds of HAS-ZF17-4448, which comprises the increased disease resistance loci on chromosome 8 from the internal resistant breeding line, as described herein. The deposit was made with the American Type Culture Collection (ATCC), 10801 University Boulevard, Manassas, Va. 20110-2209 USA. The deposit is assigned ATCC Accession No. PTA-124434, and the date of deposit was Aug. 30, 2017. Access to the deposit will be available during the pendency of the application to persons entitled thereto upon request. The deposit will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLE 1

Screening for CMV Resistance in Pepper

Phenotypically, resistance to CMV can be determined using a seedling assay in which CMV is mechanically inoculated. Inoculum can be generated from a susceptible host plant where the CMV infection has been allowed to develop for 2-3 weeks. To make inoculum, one harvests symptomatic leaves and grinds these using for example a cold pestle and mortar, or a chilled blender for larger quantities containing 0.05M phosphate buffer set to pH 7.0. Remaining bits of leaf material are removed by filtering the suspension through four layers of cheesecloth. The inoculum is kept on ice, also during inoculation. 1% diatomaceous earth is added to the inoculum as an abrasive for the mechanical inoculation. For the assay 2-3-week-old seedlings are used. The cotyledons and the second true leaf are inoculated. Before inoculation, the seedlings must be kept in the shade for 6-8 hours (50% sunlight). The seedlings are inoculated by rubbing a cotton swap that has been dipped in the inoculum on the cotyledons and the second true leaf. The leaves are rinsed immediately with water after inoculation. Following the inoculation, the plants are kept in the shade for another day to prevent damage from sunlight and to increase infection frequency. For the rest of the experiment, the seedlings are maintained in a greenhouse with 25-35° C. during the day and 22-28° C. during the night. Fertilizer is applied once a week and the plants can be treated with pesticides if necessary. Symptoms should develop within 10-14 days, which include green vein banding, mosaic or mottle on the leaves, deformation and sometimes dwarfing. The disease reaction is measured 3 weeks after inoculation and should be completed within 1-2 days. Leaf symptoms are scored on a 1-9 scale, where 1 means no symptoms on the plant and a 9 represents a high level of systemic symptoms with dwarfing and/or necrosis. In between scores are 3, which is given to plants with mild symptoms on the lower leaves, 5, which is given to plants with more symptoms on the lower and middle leaves, 7, which is given to plants with systemic symptoms and dwarfing. Plants scoring 1-3 are considered resistant, while plants scoring 7-9 are considered susceptible with the plants scoring in between are considered intermediate resistant. To determine the resistance level of a genotype it is necessary to include at least 20 plants per genotype in the experiment. For the control lines, however, it is sufficient to include 5 plants per control. Each experiment should contain at least a susceptible, ideally one that is susceptible to all CMV and one that contains the chromosome 2 resistance locus, and resistant control to ensure that the infection procedure was successful. A resistant control is for example HAS-ZF17-4448, while, e.g., Bukang or California Wonder can be used as susceptible controls. Note that these are examples of control lines and that other plant lines can be used as controls if they consistently fall within a certain score group.

EXAMPLE 2

Identification of the Resistance Locus on Chromosome 8

A set of 29 pepper lines were tested for resistance to rbCMV, which resulted in the identification of an internal resistant breeding line. This line was subsequently crossed with CMV sensitive pepper lines to identify the QTL conferring rbCMV resistance and test the efficacy of the resistance in other genetic backgrounds.

An initial mapping population was created using a cross between the first internal susceptible breeding line and the internal resistant breeding line. The F2:F3 population was used to map resistance QTLs. The $F_3$ population was exposed to the resistance breaking CMV isolate "Bucheon"

and a major QTL was discovered on chromosome 8. To validate the location of the resistance, a DH population was created by crossing a third internal susceptible breeding line (CMV sensitive) to the internal resistant breeding line. The DH lines were genotyped using a wide range of markers and scored for resistance to the rbCMV "Bucheon" isolate. Again, a significant QTL (FIG. 1) was discovered on the proximal end of chromosome 8, as can be visualized in the graph with LOD score values (Y-axis) plotted along the length of the chromosome (X-axis).

Figure 2A:
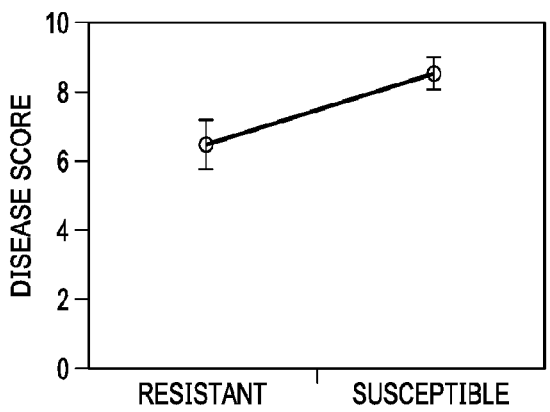
FIG. 2A. The presence of the resistance QTL on chromosome 8 significantly reduces the disease score to intermediate resistance when tested against a CMV isolate that breaks the resistance locus on chromosome 2.
Figure 2B:
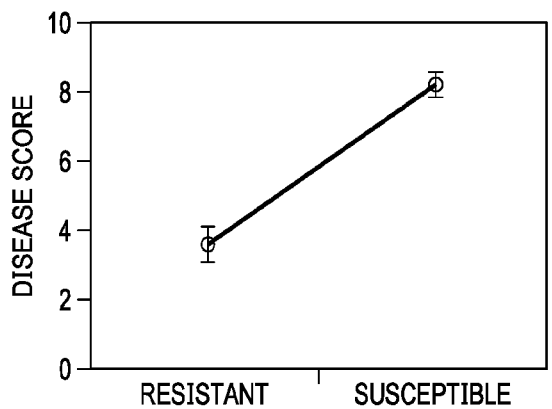
FIG. 2B. The presence of the resistance QTL on chromosome 8 significantly reduces the disease score to high resistance when tested against a that cannot break the resistance locus on chromosome 2.
Figure 2C:
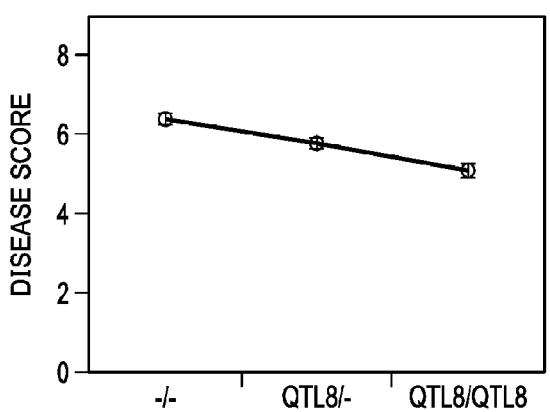
FIG. 2C. Additive resistance is observed when the QTL of chromosome 8 is introgressed into a first internal rbCMV susceptible breeding line.
Figure 2D:
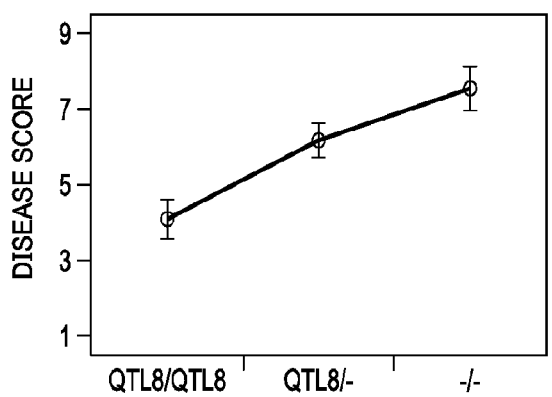
FIG. 2D. Additive resistance is observed when the QTL of chromosome 8 is introgressed into a second internal rbCMV susceptible breeding line.
Figure 3:
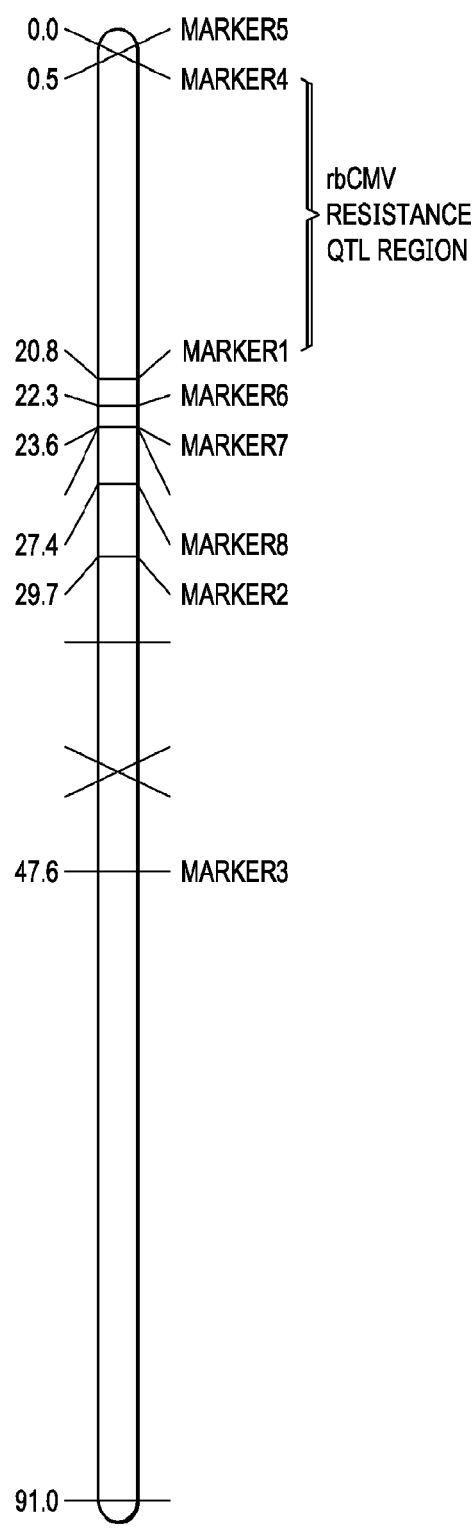
FIG. 3: Overview of marker positions and chromosomal region that confers rbCMV resistance on chromosome 8 based on the fine mapping results.

Testing of the resistance QTL revealed not only that introgressing the allele results in significantly reduced level of infection by rbCMV isolates (FIG. 2A), but also significantly reduces the infection of "normal" CMV isolates (FIG. 2B). Finally, it was confirmed in several susceptible backgrounds (internal susceptible breeding lines 1 and 2) that the resistance QTL on chromosome 8 is additive (FIG. 2C and FIG. 2D).

Mapping of the resistance locus has been problematic as it was found that the tip of chromosome 8 where the QTL is located has a reduced recombination rate. Physical and genetic analysis revealed that the tip contained a small genetic region, but a very large physical region, suggesting that the locus is near the centromere of chromosome 8. Nevertheless, it was possible to find SNP markers associated with the QTL.

For further fine mapping of the locus, an additional set of markers was developed based on the public genome of pepper (Pepper CM334v.1.55). Five new markers, Marker4, Marker5, Marker6, Marker7, and Marker8, were located between Marker3 and the uncharted distal chromosome end based on the pepper genome sequence. In addition, a $BC_4F_2$ mapping population segregating for resistance was developed using 154 recombinant families. This population was evaluated based on the level of rbCMV resistance in multiple locations using a complete block design with the recurrent parent as the susceptible control and the resistance donor as resistant control. Simultaneously, the plants were genotyped using the new marker set. Surprisingly, it was found that the expected order of markers, which was based on the public genome sequence, did not correspond to the genetic map generated from the segregating population. This result shows that the current version of the pepper genome is not accurate in this region of chromosome 8, which makes reliable marker development extremely difficult. Nevertheless, it was possible to more accurately define the CMV resistance locus, which is located between Marker1 and Marker4 (FIG. 3). This region is located more towards the distal end of the chromosome than the initial analysis indicated, which is likely due to an absence of markers at the chromosomal end in the original analysis. Selected markers developed for the mapping study are shown in Table 1.

Forward primer GGTTGGTTTGCTAAATGTTGAGGGTTA (SEQ ID NO:1), reverse primer CCCAGGCTTAATGAAACCTTCTTC (SEQ ID NO:2), probe 1 CTTTGCTTACACTATTTGAC (SEQ ID NO:3) and probe 2 TTGCTTACACTGTTTGAC (SEQ ID NO:4) are used with Marker1. For Marker1, the marker sequence is shown in SEQ ID NO:5. Forward primer TCAGTTGGATCTCATTTAAATGCACTAG (SEQ ID NO:6), reverse primer TTCTGAAGAGCGGTGTTGCT (SEQ ID NO:7), probe 1 AATTGGCAAGTACTACTATTA (SEQ ID NO:8) and probe 2 TGGCAAGTACTGCTATTA (SEQ ID NO:9) are used with Marker2. For Marker2, the marker sequence is shown in SEQ ID NO:10. Forward primer GGAATAGCATCAGAAATTATCAAGGCAAA (SEQ ID NO:11), reverse primer CCGCTGCGCTACTCTGATTT (SEQ ID NO:12), probe 1 AGCCAACATTTGGTATCAGA (SEQ ID NO:13) and probe 2 AGCCAACATTTGATATCAGA (SEQ ID NO:14) are used with Marker3. For Marker3, the marker sequence is shown in SEQ ID NO:15. Forward primer CCTACTTCTTCCACCTTCCCTGAT (SEQ ID NO:17), reverse primer CAGTTAACTAAACCAATCTAGTCACCGA (SEQ ID NO:18), probe 1 TGATTGTTCCTCAATATGTT (SEQ ID NO:19) and probe 2 ATTGTTCCTCGATATGTT (SEQ ID NO:20) are used with Marker4. For Marker4, the marker sequence is shown in SEQ ID NO:16.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

TABLE 1

Markers for identifying the CMV resistance locus on pepper chromosome 8.

| Marker | Position (cM) | SNP Change | SNP Position on Public Genome (bp) | Marker Sequence (SEQ ID NO) | Forward Primer (SEQ ID NO) | Reverse Primer (SEQ ID NO) | Probe 1 (SEQ ID NO) | Probe 2 (SEQ ID NO) |
|---|---|---|---|---|---|---|---|---|
| Marker4 | 0.5 | [C/T] | 2,992,472 | 16 | 17 | 18 | 19 | 20 |
| Marker1 | 19.29999924 | [A/G] | 32,904,383 | 5 | 1 | 2 | 3 | 4 |
| Marker2 | 29.79999924 | [G/A] | 123,493,570 | 10 | 6 | 7 | 8 | 9 |
| Marker3 | 47.63867188 | [C/T] | 130,014,877 | 15 | 11 | 12 | 13 | 14 |

The invention claimed is:

1. A cultivated variety of a *Capsicum annuum* plant comprising an introgressed allele on chromosome 8 that confers increased resistance to resistance-breaking cucumber mosaic virus (CMV) strains relative to a plant lacking said introgression, wherein a sample of seed comprising said allele is deposited under ATCC Accession Number PTA-124434.

2. The plant of claim 1, wherein said introgressed allele is further defined as:
   a) flanked by Marker1 (SEQ ID NO:5) and Marker4 (SEQ ID NO:16) in said plant;
   b) located between 32,904,383 bp and 2,992,472 bp of chromosome 8 in public pepper genome sequence Pepper.CM334v1.55; or
   c) comprising the resistance haplotype of HAS-ZF17-4448, wherein a sample of seed comprising said resistance haplotype was deposited under ATCC Accession Number PTA-124434.

3. The plant of claim 1, wherein a) said resistance comprises resistance to CMV isolate "Bucheon"; or b) the plant is homozygous for said introgressed allele.

4. A seed that produces the plant of claim 1.

5. A plant part of the plant of claim 1.

6. The plant part of claim 5, wherein the plant part is a cell, a seed, a root, a stem, a leaf, a fruit, a flower, or pollen.

7. A method for producing a cultivated variety of a *Capsicum annuum* plant with improved resistance to resistance-breaking cucumber mosaic virus (CMV) strains, comprising introgressing into said plant a chromosomal segment from chromosome 8 that confers resistance to resistance-breaking cucumber mosaic virus (CMV) strains relative to a plant lacking said introgression, wherein a sample of seed comprising said chromosomal segment is deposited under ATCC Accession Number PTA-124434.

8. The method of claim 7, wherein said introgressing comprises:
   a) crossing a plant comprising said chromosomal segment with itself or with a second *Capsicum annuum* plant of a different genotype to produce one or more progeny plants; and
   b) selecting a progeny plant comprising said chromosomal segment.

9. The method of claim 7, wherein selecting a progeny plant comprises:
   a) detecting at least one allele flanked by Marker1 (SEQ ID NO:5) and Marker4 (SEQ ID NO:16) on chromosome 8; or
   b) detecting Marker1 (SEQ ID NO:5) or Marker4 (SEQ ID NO:16).

10. The method of claim 8, wherein a) the progeny plant is an $F_2$-$F_6$ progeny plant; or b) said crossing comprises backcrossing.

11. The method of claim 10, wherein said backcrossing comprises from 2-7 generations of backcrosses.

12. The method of claim 7, wherein said introgressed allele comprises the resistance haplotype of HAS-ZF17-4448, wherein a sample of seed comprising said resistance haplotype was deposited under ATCC Accession Number PTA-124434.

13. A *Capsicum annuum* plant produced by the method of claim 7.

14. A method of producing food or feed comprising obtaining a plant according to claim 1, or a part thereof, and producing said food or feed from said plant or part thereof.

15. A *Capsicum annuum* plant obtainable by a method comprising the step of introgressing into a plant a resistance to resistance-breaking cucumber mosaic virus (CMV) strains allele, wherein said resistance allele is defined as located in a genomic region flanked by Marker1 (SEQ ID NO:5) and Marker4 (SEQ ID NO:16) on chromosome 8, and wherein a sample of seed comprising said resistance allele is deposited under ATCC Accession Number PTA-124434.

16. The *Capsicum annuum* plant of claim 15, wherein said introgressing comprises backcrossing, marker-assisted selection or assaying for said resistance to resistance-breaking cucumber mosaic virus (CMV) strains.

17. A method of selecting a *Capsicum annuum* plant exhibiting resistance to resistance-breaking cucumber mosaic virus (CMV) strains, comprising:
   a) crossing the *Capsicum annuum* plant of claim 1 with itself or with a second *Capsicum annuum* plant of a different genotype to produce one or more progeny plants; and
   b) selecting a progeny plant comprising said introgressed allele.

18. The method of claim 17, wherein selecting said progeny plant comprises:
   a) identifying a genetic marker genetically linked to said introgression;
   b) identifying a genetic marker within or genetically linked to a genomic region flanked in the genome of said plant by Marker1 (SEQ ID NO:5) and Marker4 (SEQ ID NO:16) on chromosome 8; or
   c) detecting Marker1 (SEQ ID NO:5) or Marker4 (SEQ ID NO:16).

19. The method of claim 17, wherein a) said progeny plant is an $F_2$-$F_6$ progeny plant; or b) producing said progeny plant comprises backcrossing.

20. A method of producing food or feed comprising obtaining a plant according to claim 13, or a part thereof, and producing said food or feed from said plant or part thereof.

\* \* \* \* \*